United States Patent [19]

Delente et al.

[11] 4,230,537
[45] Oct. 28, 1980

[54] DISCRETE BIOCHEMICAL ELECTRODE SYSTEM

[75] Inventors: Jacques J. Delente, University City; Lloyd E. Weeks, St. Louis, both of Mo.

[73] Assignee: Monsanto Company, St. Louis, Mo.

[21] Appl. No.: 642,205

[22] Filed: Dec. 18, 1975

[51] Int. Cl.² .................. G01N 27/46; G01N 31/14
[52] U.S. Cl. ................ 204/1 T; 204/195 P; 204/195 B
[58] Field of Search ............. 204/195 B, 195 P, 1 E

[56] References Cited

U.S. PATENT DOCUMENTS

| 3,098,813 | 7/1963  | Beebe et al.   | 204/195 P |
| 3,380,905 | 4/1968  | Clark          | 204/195 P |
| 3,505,195 | 4/1970  | Nielsen et al. | 204/195 P |
| 3,542,662 | 11/1970 | Hicks et al.   | 204/195 B |
| 3,700,578 | 10/1972 | Clifton et al. | 204/195 P |
| 3,718,563 | 2/1973  | Krull et al.   | 204/195 P |
| 3,718,566 | 2/1973  | Krebs          | 204/195 P |

OTHER PUBLICATIONS

Kadish et al., "Clin. Chem.", vol. 14, 1968, pp. 116–131.

*Primary Examiner*—G. L. Kaplan
*Attorney, Agent, or Firm*—Scott J. Meyer; John D. Upham

[57] ABSTRACT

A biochemical device and method for the determination of dissolved gases in solution is provided which employs a dry electrode/sample interface. Dissolved oxygen or other gas concentration in a liquid sample is measured by its diffusion through a selectively permeable membrane which is an integral part of a disposable receptacle. The receptacle makes contact with a gas-sensing electrode at the locus of the selectively permeable membrane whereby the determination of the concentration of said gas is made by the electrode without ever touching the liquid sample.

5 Claims, 2 Drawing Figures

DISCRETE BIOCHEMICAL ELECTRODE SYSTEM

BACKGROUND OF THE INVENTION

This invention relates to a biochemical device and method for the determination of dissolved gases in solution. More particularly, this invention relates to a dry electrode/sample interface for discrete clinical analysis with an oxygen-sensing electrode.

Oxygen-sensing electrodes which measure dissolved oxygen in solution are well-known. The Clark $pO_2$ electrode described in U.S. Pat. No. 2,913,386 is typical. In this electrode, oxygen diffuses through a gas-permeable membrane and is reduced at a platinum cathode which is kept at a fixed potential with respect to a silver-silver chloride reference anode.

Such electrodes have been used for a variety of biochemical determinations useful in clinical diagnosis. For example, the determination of blood glucose levels has been made with an oxygen-sensing electrode by measuring the oxygen uptake in a glucose oxidase enzyme catalyzed reaction. Illustrative of such use of the Clark $pO_2$ electrode are the report by Kunz and Stastny, *Clin. Chem.* 20, 1018-22 (1974) and the review article by Gough and Andrade, *Science* 180, 380-84 (1973).

In use of the oxygen-sensing electrode, the sample reagent solution to be analyzed comes into contact with the electrode through a plastic membrane which is permeable to oxygen but impermeable to water and electrolytes. The desirability of constructing the electrode so that the membrane precludes any contact between the reagent sample to be analyzed and the electrolyte has been recognized heretofore. This is generally accomplished by forming a barrier with the membrane which is held in place at one end of the electrode with O-rings as described, for example, in U.S. Pat. Nos. 2,912,386 and 3,542,662, or sealingly positioned over the electrolyte chamber as disclosed in U.S. Pat. No. 3,334,039, or clamped in mounting discs as taught in U.S. Pat. No. 3,445,369. However, in these oxygen-sensing devices, the electrode still comes into contact with the reagent sample. A system whereby the electrode does not come into contact with the reagent sample would provide the advantage of freedom from sample carryover onto the electrode, and thereby, eliminate problems of cross contamination and need for washing after every sample analysis.

BRIEF SUMMARY OF THE INVENTION

In accordance with the present invention a biochemical device and method for the determination of dissolved gases in solution is provided which employs a dry electrode/sample interface. In this system, the dissolved oxygen or other gas concentration is measured by its diffusion through a membrane which is an integral part of a disposable receptacle. The sample to be analyzed and the reagents are placed in the receptacle. When the oxygen-sensing or other gas-sensing electrode touches the outside of the receptacle membrane, mass transfer of dissolved gas takes place toward the electrode, thereby providing means for determination of the sample oxygen or other gas by the electrode without ever touching the sample.

DETAILED DESCRIPTION OF THE INVENTION

In the present invention, several variations of the electrode system for discrete biochemical analysis are contemplated by the inventors. While the specification concludes with claims particularly pointing out and distinctly claiming the subject matter regarded as forming the present invention, it is believed that the invention and its advantages will be better understood from the following description of the preferred embodiments taken in connection with the accompanying drawings in which:

Figure 1:
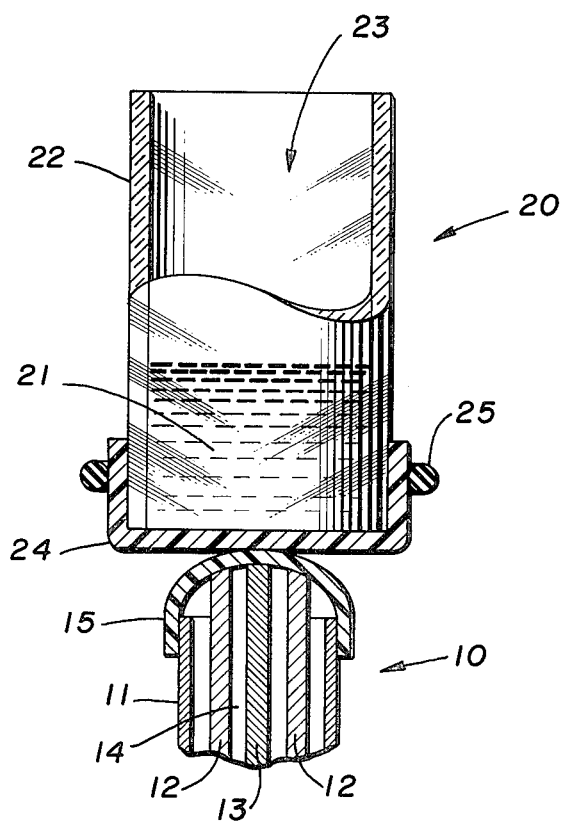
FIG. 1 is a fragmentary elevation in cross section illustrating an embodiment of the invention.

Turning now to the drawings, reference numeral 10 refers generally to a conventional oxygen-sensing electrode which is only partially illustrated as will suffice to show the connection of the invention therewith. Electrode 10 is essentially a tubular body defining a chamber 11. Within this chamber is an anode 12, a cathode 13 and an electrolyte solution 14. Chamber 11 is sealingly closed at the upper end with a selectively permeable membrane 15. The anode-cathode materials can be, for example, any noble metal cathode such as gold, silver or rhodium in conjunction with a zinc, cadmium or lead anode. The electrolyte solution is a conventional ionic conductor for carrying current, for example, an aqueous buffered solution containing a halide salt. Membrane 15 can be made of a plastic material permeable to oxygen and impermeable to water and electrolytes such as, for example, Teflon (duPont polytetrafluoroethylene), polyethylene, polypropylene, polystyrene, polyvinyl chloride and silicone rubber. In use, the electrode terminals are attached to a recorder (not shown) for indicating the electrode output.

Reference numeral 20 refers generally to a cuvette for holding the reagents 21 and the liquid sample to be analyzed. Cuvette 20 is essentially a container with sidewalls 22 which can be, for example, cylindrical as in an ordinary test tube or rectangular as in a conventional sample cuvette for spectrophotometric analysis. As can be seen, cuvette 20 is open at the top 23 for introduction of liquids or other substances for the test. The bottom of cuvette 20 is sealingly closed with a membrane 24 which is permeable to oxygen or other gases but impermeable to water and liquid reagents. Membrane 24 can be made of the same selectively permeable materials as used for membrane 15 in the electrode.

In FIG. 1 of the drawings, membrane 24 is shown to be secured across the bottom of cuvette 20 with an O-ring seal 25. Other means of retaining membrane 24 on the cuvette can be employed, for example, solvent sealing, or other portions of the cuvette such as in the sidewall, or even the entire cuvette, can be comprised of the membrane material, if desired. While the sidewalls of the cuvette preferably will have a sufficient rigidity to be manually held such as provided by glass or a rigid plastic material such as polystyrene or acrylic, the bottom or other membrane portion of the cuvette which touches the oxygen-sensing electrode will have a thickness such as to facilitate the rapid diffusion of oxygen across its walls. For example, a relatively thin flexible silicone sheet having a thickness ranging from about one to about ten mils is suitable for the membrane.

In the foregoing embodiment which comprises a two-membrane system, one membrane holds the electrolyte against the electrode metals while the second membrane holds the sample in the cuvette. When the two membranes are brought together, as shown in FIG.

1, oxygen diffuses through both membranes. In this embodiment there is no need to renew the electrolyte between individual sample measurements, and the entire operation is dry except for the sample.

In another embodiment of the invention, the system employs only one membrane, namely the cuvette membrane. In this embodiment, the electrolyte generally is replaced with each test and the electrode metals are in direct contact with the cuvette membrane. While the latter embodiment provides greater sensitivity through a faster response and a larger signal than the two-membrane embodiment, it involves a less convenient handling of electrolyte which is a corrosive solution.

Both of the foregoing illustrative embodiments of the discrete biochemical electrode system have the distinct advantage of complete freedom from cross contamination and carryover of sample since the electrode does not touch the liquid sample. Thus, there is no need for washing of the electrode between individual sample assays. Another advantage, particularly when the electrode sensing is carried out at the bottom of the sample receptacle, is that very small samples can be used, for example, 1 to 5 microliters ($\mu l$), and very small amounts of test reagents can be employed, for example, on the order of 50 $\mu l$. In conventional gas sensing electrode systems used heretofore, it has been necessary to immerse the electrode in the sample solution and, thus, larger quantities of materials have been required. The sample receptacle with the component membrane as employed in the present invention can be an inexpensive, completely disposable cuvette or similar such container and, thereby, entirely eliminate the need for cleaning and drying which is necessary in conventional gas sensing electrode systems.

The present invention also lends itself to automated biochemical analysis. For example, a plurality of cuvettes can be arranged on a turntable, or other such rotatable device, and brought into juxtaposition for interfacing with the gas sensing electrode at predetermined timed intervals. In yet another embodiment, an elongated membrane tape can be passed across the tip of the electrode as a moving belt. Indentations can then be mechanically formed, or can be preformed, in the membrane tape at spaced intervals to thereby provide sample receptacles for interfacing with the electrode. Automated pipetting also can be employed for handling of the test samples and reagents in these embodiments.

Use of the discrete biochemical electrode system of this invention is illustrated by the determination of blood glucose levels according to the following reaction:

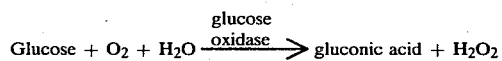

Background information on the use of a conventional oxygen electrode for determining glucose in accordance with this reaction can be had by reference to Kadish et al, *Clin. Chem.* 14, 116–131 (1968). In accordance with the present invention, the sample, which contains glucose and oxygen, is placed in the cuvette as described herein together with glucose oxidase in a buffered reagent solution. When an oxygen-sensing electrode is placed in contact with the cuvette membrane, the decrease in the diffusion of oxygen across the membrane is proportional to the oxygen consumed in the enzyme catalyzed oxidation reaction and produces a linear response in the electrode output which can be followed on an attached recorder. The reagent system preferably is agitated to facilitate mixing and oxygen diffusion. This can be carried out, for example, by mounting the cuvette or the electrode on a conventional vibrator.

Figure 2:
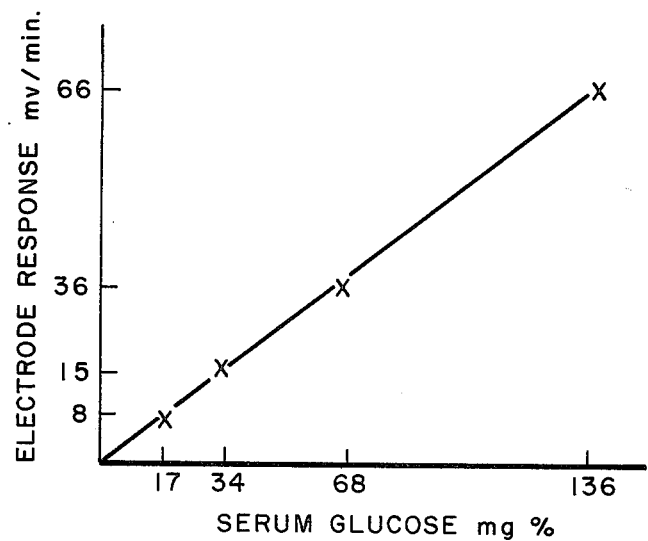
FIG. 2 is a curve which graphically portrays the response in a typical assay with the invention.

FIG. 2 of the drawings shows the substantial linearity of electrode response in millivolts per minute plotted against glucose concentration in milligram percent (milligrams per 100 ml) in a typical example of the invention. In this example, one ml of glucose oxidase (Fermco Laboratories Ovazyme XX, 1650 I.U./ml, diluted with 5 volumes of buffered iodine-iodide-molybdate solution, pH 6, and 0.3 volumes ethanol) was added to a cuvette, as illustrated in FIG. 1, having a silicone rubber membrane (Dow Corning Silastic 380) one mil thick, at the bottom. The electrode was allowed to equilibrate (which took about two minutes) to establish a base line for the oxygen-sensing electrode determination of glucose. Then, 100 microliters of Stattrol serum (Worthington Biochemical Corp. control serum containing glucose) was added and the electrode output was recorded. This was repeated for four aqueous dilutions containing, respectively, 17, 34, 68 and 136 milligram percent glucose.

The oxygen-sensing electrode employed in this example was a modification of the membrane electrode described by Elsworth, *The Chemical Engineer*, February 1972, pp. 63–71. This modification employed a silver cathode, a lead anode, and electrolyte consisting of 5.0 M acetic acid, 0.5 M sodium acetate and 0.1 M lead acetate. A Beckman recorder attached to the electrode terminals indicated the electrode output. In this electrode, the reaction at the silver cathode is believed to be

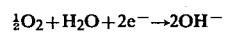

while at the lead anode the loss of electrons produces lead ions.

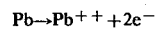

The lead ions combine with hydroxyl to form lead hydroxide on the anode surface to result in an overall reaction as follows:

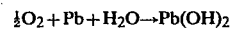

With acetate as the electrolyte, a deposit of basic lead acetate builds up on the lead surface and lead salts accumulate in the electrolyte. The expendable materials thereby are the lead anode and the acetate of the electrolyte.

The discrete biochemical electrode system of this invention is adaptable to many uses and a wide variety of other tests in which oxygen, ammonia, carbon dioxide or other gases are present or are released or consumed by a biochemical reaction. For example, the diffusion of dissolved oxygen in solution can be determined in biochemical tests for lactate dehydrogenase, creatine phosphokinase, dopamine-$\beta$-hydroxylase, cholesterol and serum triglycerides. The diffusion of ammonia can be determined in a biochemical test for blood urea and the diffusion of carbon dioxide can be determined in a biochemical test for pyruvate. Suitable reagent systems for these biochemical determinations are illustrated as follows:

Lactate Dehydrogenase $$\text{lactate} + NAD^+ \xrightleftharpoons{LDH} \text{pyruvate} + NADH + H^+ \quad (1)$$

$$NADH + H^+ + \tfrac{1}{2} O_2 \xrightleftharpoons{\substack{\text{electron} \\ \text{transfer} \\ \text{agent}}} NAD^+ + H_2O \quad (2)$$

Creatine Phosphokinase $$\text{creatine phosphate} + ADP \xrightleftharpoons{CPK} \text{creatine} + ATP \quad (1)$$

$$ATP + \text{glucose} \xrightleftharpoons{HK} \text{G-6-P} + ADP \quad (2)$$

$$\text{G-6-P} + NADP^+ \xrightleftharpoons{\text{G-6-PDH}} \quad (3)$$

$$\text{6-phosphogluconate} + NADPH + H^+ \quad (4)$$

$$NADPH + H^+ + \tfrac{1}{2} O_2 \xrightleftharpoons{\substack{\text{electrode} \\ \text{transfer} \\ \text{agent}}} NADP^+ + H_2O$$

Dopamine-β-Hydroxylase $$\text{tyramine} + \text{ascorbate} + O_2 \xrightarrow[\text{fumarate}]{D\beta H} $$
$$\text{octopamine} + H_2O + \text{dehydroascorbate}$$

Cholesterol $$\text{cholesterol} + \tfrac{1}{2} O_2 + H_2O \xrightarrow{\substack{\text{Cholesterol} \\ \text{oxidase}}} $$
$$\text{cholest-4-en-3-one} + H_2O_2$$

Triglycerides $$\text{triglycerides} \xrightarrow{\substack{\text{lipolitic} \\ \text{enzyme}}} \text{glycerol} + \text{free fatty acids} \quad (1)$$

$$\text{glycerol} + ATP \xrightarrow{GK} \alpha\text{-GP} \quad (2)$$

$$\alpha\text{-GP} + NAD^+ \xrightarrow{\alpha\text{-GPDH}} \quad (3)$$

$$\text{dihydroxyacetone phosphate} + NADH + H^+ \quad (4)$$

$$NADH + H^+ + \tfrac{1}{2} O_2 \xrightarrow{\substack{\text{electron} \\ \text{transfer} \\ \text{agent}}} NAD^+ + H_2O$$

Urea $$\text{urea} + 2H_2O + H^+ \xrightarrow{\text{urease}} 2NH_4^+ + HCO_3^- \xrightarrow[\text{pH 10}]{NaOH} NH_3$$

Pyruvate $$\text{pyruvate} \xrightarrow{\substack{\text{pyruvate} \\ \text{decarboxylase}}} $$
$$\text{acetaldehyde} + HCO_3^- \xrightarrow[\text{pH 2-3}]{HCl} CO_2$$

In the foregoing tests for lactate dehydrogenase, creatine phosphokinase, dopamine-β-hydroxylase, cholesterol and triglycerides, the uptake of oxygen by the reactions is measured in the same way that the consumption of oxygen is measured in the test for glucose. That is, when the oxygen-sensing electrode is placed in contact with the cuvette membrane, the decrease in the diffusion of oxygen across the membrane is proportional to the oxygen consumed in the reactions and produces a linear response in electrode output. Conversely, in the above tests for urea and pyruvate, the release of ammonia and carbon dioxide, respectively, in the reactions is determined by the increase in diffusion of these gases across the membrane with gas-sensing electrodes for ammonia and carbon dioxide. A suitable gas-sensing electrode for ammonia is commercially available from Orion Research Incorporated and a suitable gas-sensing electrode for carbon dioxide is commercially available from the Sensorex subsidiary of Bentley Laboratories Inc.

The components of the reagents used in the discrete biochemical analysis system of this invention such as, for example, enzymes and coenzymes, can be part of the liquid medium in the receptacle, which can be freeze dried, or they can be bound to the membrane by well-known immobilization methods. Thus, the enzymes and other reagent components can be applied to the cuvette in solution form and then freeze-dried and the cuvette sealed to provide a shelf-stable, readily usable container to which only water or buffer and the test sample need be added prior to the gas-sensing electrode assay. Or, if desired, enzymes employed in the reagent can be attached to the membrane itself. For example, a film of nylon-silicone block copolymer with partial surface hydrolysis to generate amino groups can be used to supply functional groups to attach enzymes. Such attachments can be made by use of conventional carbodiimide reagents. Again, it is then necessary to add only water or buffer and the test sample to the cuvette prior to the assay with the electrode.

Still other embodiments of the invention and various changes and modifications to the foregoing embodiments will be apparent to the person skilled in the art after reading this disclosure and the appended claims and it is intended to include within the scope of the appended claims all such embodiments, changes and modifications as come within the spirit and scope of the invention.

What is claimed is:

1. A method for discrete biochemical analysis employing the determination of the concentration of a dissolved gas in solution with a gas-sensing electrode, said electrode comprising an anode, cathode, electrolyte solution and a selectively permeable membrane enclosure at one end, said method comprising causing the diffusion of said gas across a selectively permeable membrane portion of a sample receptacle containing a liquid biochemical component of a body fluid to be determined as a recognized adjunct of clinical diagnosis, said sample receptacle membrane having a dry interface with said electrode membrane at the locus of said gas diffusion whereby the liquid in said sample receptacle does not come into contact with any part of said electrode and said electrolyte solution does not come into contact with any part of said sample receptacle during said gas diffusion.

2. The method of claim 1 in which the gas is oxygen.

3. The method of claim 1 in which the membranes are silicone rubber.

4. The method of claim 1 in which the biochemical analysis comprises an enzyme catalyzed reaction.

5. The method of claim 1 in which the sample receptacle membrane is sealingly secured across the bottom of said receptacle.

* * * * *